United States Patent [19]

Campbell et al.

[11] Patent Number: 4,460,585
[45] Date of Patent: Jul. 17, 1984

[54] 1-ARYL-4-HYDRAZINYL-S-TRIAZIN-2-ONES

[75] Inventors: Henry F. Campbell; Thomas H. Scholz, both of Lansdale; George H. Douglas, Malvern, all of Pa.

[73] Assignee: William H. Rorer, Inc., Fort Washington, Pa.

[21] Appl. No.: 458,451

[22] Filed: Jan. 17, 1983

Related U.S. Application Data

[63] Continuation-in-part of Ser. No. 280,816, Jul. 6, 1981, abandoned.

[51] Int. Cl.$^3$ ............... C07D 251/16; C07D 251/42; A61K 31/53
[52] U.S. Cl. .................................. 424/249; 544/211
[58] Field of Search ..................... 544/211; 424/249

[56] References Cited

U.S. PATENT DOCUMENTS 4,246,409  1/1981  Douglas et al. ............... 544/211
4,338,441  7/1982  Douglas et al. ............... 544/211
4,406,897  9/1983  Campbell et al. ............. 544/211

Primary Examiner—John M. Ford
Attorney, Agent, or Firm—James A. Nicholson; Alexis Barron; Martin F. Savitzky

[57] ABSTRACT

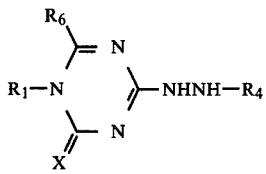

This invention relates to 1-aryl-4-hydrazinyl-1,2-dihydro-1,3,5-triazin-2-ones and 2-thiones of Formula I, processes for their preparation, isobiuret and 4-alkoxy-s-triazinone preparative intermediates, and methods of treating physiological disorders in humans and animals, in particular, cardiovascular disorders, including hypertension.

8 Claims, No Drawings

1-ARYL-4-HYDRAZINYL-S-TRIAZIN-2-ONES

This is a continuation-in-part application of Ser. No. 280,816, filed July 6, 1981, now abandoned.

FIELD OF THE INVENTION

This invention relates to s-triazin-2-one and thione compounds, processes for their preparation, intermediates useful in their preparation, pharmaceutical compositions and methods for influencing physiological function, such as blood pressure, in humans and animals.

REPORTED DEVELOPMENTS 1,3,5-triazine compounds are known to possess a broad spectrum of biological activity. The 4,6-diamino-1,2-dihydro-2-triazines have been reported to be effective as antimalarial, antitumor, antihelminthic and antibacterial agents as well as active agents against coccidiosis in chicks and against murine toxoplasmosis. See *Heterocyclic Compounds*, Volume 7, John Wiley & Sons, 1961 (Elderfield ed.) Chapter 8, "S-Triazines."

The antiherbicidal activity of 1-alkyl-4-alkylamino-1,2-dihydro-2-triazin-2-ones and thiones has been reported in U.S. Pat. No. 3,585,197 to Seidel et al. Recently, 1-aryl-1,2-dihydro-1,3,5-triazin-2-ones (thione) and their pharmacological uses have been reported in U.S. Pat. No. 4,246,409 to Douglas et al.

S-Triazin-2-ones (thiones) which are substituted by hydrazinyl groups in the 4-position have not been previously reported.

SUMMARY OF THE INVENTION

This invention relates to a class of s-triazine compounds according to Formula I

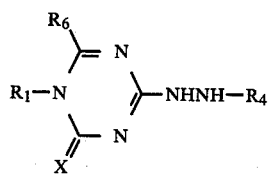

wherein:

X is oxygen or sulfur;

$R_1$ is aryl, substituted aryl, aralkyl, heterocyclic, substituted heterocyclic, heterocyclic lower alkyl, or substituted heterocyclic lower alkyl;

$R_4$ is hydrogen, alkyl, cycloalkyl, alkenyl, alkynyl, alkanoyl, carboalkoxy, carbamoyl, alkyl carbamoyl, aryl, aroyl, aralkyl, heterocyclic, substituted heterocyclic, halo alkyl, or halo alkanoyl;

$R_6$ is hydrogen, alkyl, cycloalkyl, alkenyl, alkynyl or aralkyl; and the pharmaceutically acceptable acid addition salts thereof.

This invention relates also to processes for the preparation of compounds of Formula I and intermediate compounds useful in these processes.

Compounds within the scope of Formula I possess pharmaceutical activity, including cardiovascular activity, such as blood pressure lowering activity, and are useful in methods of treating physiological disorders, such as hypertension, in humans and animals.

DETAILED DESCRIPTION OF THE INVENTION

Depending upon the specific substitution, compounds of Formula I above may be present in enolized or tautomeric forms. Certain of the compounds can also be obtained as hydrates or in different polymorphic forms. The structures used herein to designate novel compounds are intended to include the compound along with its alternative or transient states. The nomenclature generally employed to identify the novel triazine derivatives as disclosed herein is based upon the ring structure shown in Formula I with the triazine ring positions numbered counterclockwise beginning with the nitrogen having the $R_1$ substitution.

Compounds of this invention which are preferred include those wherein:

X is oxygen or sulfur;

$R_1$ is phenyl or substituted phenyl;

$R_4$ is hydrogen, lower alkyl, lower alkanoyl, carboloweralkoxy, phenyl, or benzoyl;

$R_6$ is hydrogen or lower alkyl; and the pharmaceutically acceptable acid addition salts thereof.

A subclass of these compounds, of particular interest, includes compounds according to Formula I wherein:

X is oxygen or sulfur;

$R_1$ is phenyl or phenyl in which one or more of the phenyl hydrogens has been replaced by the same or different substituents selected from the group consisting of halo or lower alkyl;

$R_4$ is hydrogen;

$R_6$ is hydrogen or methyl; and the pharmaceutically acceptable acid addition salts thereof.

Another class of preferred compounds is where:

$R_1$ is phenyl, 2-halophenyl, 3-halophenyl, 4-halophenyl, 3,4-dihalophenyl, 3-trihalomethylphenyl or 2,6-diloweralkylphenyl;

$R_4$ is lower alkanoyl, benzoyl, or carboloweralkoxy;

$R_6$ is hydrogen; and the pharmaceutically acceptable acid addition salts thereof.

A further preferred class of compounds is where:

$R_1$ is phenyl or substituted phenyl;

$R_4$ is methyl; and $R_6$ is hydrogen;

provided that when $R_1$ is substituted phenyl the phenyl substituent is either 3- or 4-halo, or 3-trihalo alkyl; and the pharmaceutically acceptable acid addition salts thereof.

A special embodiment of these preferred classes of compounds is where:

$R_1$ is phenyl substituted in either the meta or para positions by a halogen, for example, chloro; or where $R_1$ is phenyl substituted in either or both of the meta or para positions by chloro when $R_4$ is other than methyl.

Another special embodiment of these preferred classes of compounds is where:

$R_1$ is phenyl, 4-loweralkyl phenyl or 4-loweralkoxy phenyl;

$R_6$ is hydrogen; and $R_4$ is phenyl; and the pharmaceutically acceptable acid addition salts thereof.

An embodiment of this invention, of particular interest, is a 4-hydrazinyl traizinone according to Formula I wherein $R_1$ is a heterocyclic ring. The most preferred heterocyclic ring is pyridyl, and the exemplary subclass of the compounds according to this invention which includes the pyridyl ring is shown below in Formulae II–IV.

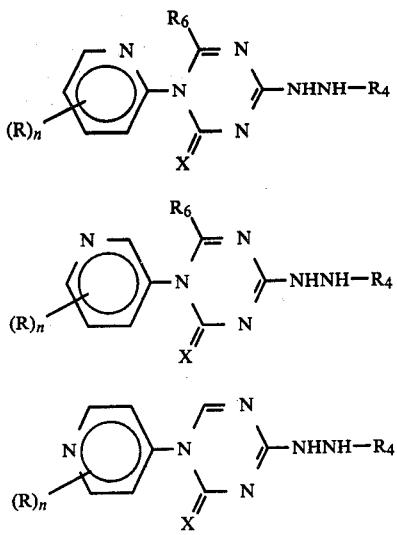

wherein:
n is zero to four;
R is alkyl, alkoxy, halo, cyano, amino, carbamoyl, alkylamino, or dialkylamino; and
X, R₄ and R₆ are as defined above.

The most preferred compounds according to this invention are listed in the following Table I.

TABLE I

| Name | M.P. |
| --- | --- |
| 4-acetylhydrazino-1-phenyl-1,2-dihydro-1,3,5-triazin-2-one | 158° C. |
| 4-ethoxycarbonylhydrazino-1-phenyl-1,2-dihydro-1,3,5-triazin-2-one | 165–167° C. |
| 4-hydrazino-1-phenyl-1,2-dihydro-1,3,5-triazin-2-one | >245° C. |
| 4-methylhydrazino-1-phenyl-1,2-dihydro-1,3,5-triazin-2-one | 182.5–133° C. |
| 4-acetylhydrazino-1-(4-chlorophenyl)-1,2-dihydro-1,3,5-triazin-2-one | 176–178° C. |
| 4-benzoylhydrazino-1-(4-chlorophenyl)-1,2-dihydro-1,3,5-triazin-2-one | 193–195° C. |
| 1-(4-chlorophenyl)-4-ethoxycarbonylhydrazino-1,2-dihydro-1,3,5-triazin-2-one | 194–195° C. |
| 1-(4-chlorophenyl)-4-hydrazino-1,2-dihydro-1,3,5-triazin-2-one | >250° C. |
| 1-(4-chlorophenyl)-4-methylhydrazino-1,2-dihydro-1,3,5-triazin-2-one | 228–231° C. |
| 4-acetylhydrazino-1-(3-chlorophenyl)-1,2-dihydro-1,3,5-triazin-2-one | 140–144° C. |
| 1-(3-chlorophenyl)-4-hydrazino-1,2-dihydro-1,3,5-triazin-2-one | >250° C. |
| 1-(3-chlorophenyl)-4-methylhydrazino-1,2-dihydro-1,3,5-triazin-2-one | 219–221° C. |
| 4-hydrazino-1-(4-methylphenyl)-1,2-dihydro-1,3,5-triazin-2-one | >250° C. |
| 1-(4-methylphenyl)-4-phenylhydrazino-1,2-dihydro-1,3,5-triazin-2-one | 196° C. |
| 1-(2,6-dichlorophenyl)-4-hydrazino-1,2-dihydro-1,3,5-triazin-2-one | >250° C. |
| 4-acetylhydrazino-1-(2-chlorophenyl)-1,2-dihydro-1,3,5-triazin-2-one | 210° C. |
| 1-(2-chlorophenyl)-4-hydrazino-1,2-dihydro-1,3,5-triazin-2-one | >250° C. |
| 1-(3,4-dichlorophenyl)-4-hydrazino-1,2-dihydro-1,3,5-triazin-2-one | >250° C. |
| 4-acetylhydrazino-1(3-dichlorophenyl)- | 183–185° C. |
| 4-methylhydrazino-1-(3-trifluoromethylphenyl)-1,2-dihydro-1,3,5-triazin-2-one | 199–201° C. |
| 4-acetylhydrazino-1-(3-trifluoromethylphenyl)-1,2-dihydro-1,3,5-triazin-2-one | 142.5–164° C. |
| 4-hydrazino-6-methyl-1-phenyl-1,2-dihydro-1,3,5-triazin-2-one | >250° C. |
| 1-(4-methylphenyl)-4-phenylhydrazino- | 196° C. |

TABLE I-continued

| Name | M.P. |
| --- | --- |
| 1,2-dihydro-1,3,5-triazin-2-one 1-(4-methoxyphenyl)-4-phenylhydrazino-1,2-dihydro-1,3,5-triazin-2-one | 170.5–171.5° C. |

As employed above and throughout the disclosure, the following terms, unless otherwise indicated, shall be understood to have the following meanings:

"Alkyl" means a saturated aliphatic hydrocarbon which may be either straight- or branched-chain. Preferred are lower alkyl groups which have up to about 6 carbon atoms, including methyl, ethyl and structural isomers of propyl, butyl, pentyl and hexyl.

"Cycloalkyl" means a saturated cyclic hydrocarbon, preferably having about 3 to about 6 carbon atoms, which may also be substituted with a lower alkyl group.

"Carbamoyl" means a radical of the formula

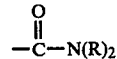

where R may be hydrogen or lower alkyl.

"Alkenyl" means an unsaturated aliphatic hydrocarbon which may include straight or branched chains. Preferred groups have up to about 6 carbon atoms and may be vinyl and any structural and geometric isomers of propenyl, butenyl, pentenyl, and hexenyl.

"Alkynyl" means an unsaturated aliphatic hydrocarbon containing one or more triple bonds. Preferred groups contain up to about 6 carbon atoms and include ethynyl, propynyl, butynyl, pentynyl, and hexynyl.

"Aryl" means a radical of an aromatic group. The preferred aromatic groups are phenyl and substituted phenyl.

"Substituted phenyl" means a phenyl group in which one or more of the hydrogens has been replaced by the same or different substituents including halo, lower alkyl, halo lower alkyl, amino, acylamino, hydroxy, phenyl lower alkoxy, lower alkanoyl, carboloweralkoxy, acyloxy, cyano, halo lower alkoxy or lower alkyl sulfonyl.

"Aralkyl" means lower alkyl in which one or more hydrogens is substituted by aryl (preferably phenyl or substituted phenyl). Preferred groups are benzyl or phenethyl.

"Heterocyclic" or "heterocyclic ring" means a cyclic or bicyclic system having 1 to 3 hetero atoms which may be nitrogen, oxygen or sulfur, including oxazolidinyl, thiazolidinyl, pyrazolidinyl, imidazolidinyl, piperidyl, piperazinyl, thiamorpholinyl, 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 5-imidazole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, carbazole, trimethyleneethylenediaminyl, ethyleneiminyl and morpholinyl;

"Substituted heterocyclic" or "substituted heterocyclic ring" means a heterocycle in which one or more of the hydrogens on the ring carbons have been replaced by substituents as given above with respect to substituted phenyl.

Preferred heterocyclic rings are pyridyl, pyrimidyl, pyrazolyl, imidazolyl, furyl, thienyl, oxazolyl, thiazolyl, piperidyl, morpholinyl, oxazolidinyl, thiazolidinyl, pyrazolidinyl, imidazolidinyl, piperazinyl, thiamorpholinyl, trimethyleneethylenediaminyl and ethyleneiminyl.

The terms "halo" and "halogen" include all four halogens, namely, fluorine, chlorine, bromine and iodine. The halo alkyls, halophenyl and halo-substituted pyridyl include groups having more than one halo substituent which may be the same or different such as trifluoromethyl, 1-chloro-2-bromo-ethyl, chlorophenyl, 4-chloropyridyl, etc.

"Acyloxy" means an organic acid radical of lower alkanoic acid such as acetoxy, propionoxy, and the like.

"Lower alkanoyl" means the acyl radical or a lower alkanoic acid, including acetyl, propionyl, butyryl, valeryl, and stearoyl.

"Alkoxy" means the oxy radical of an alkyl group, preferably a lower alkyl group, such as methoxy, ethoxy, n-propoxy, and i-propoxy.

"Aroyl" means a radical of the formula

wherein R is aryl. Preferred aroyl groups include benzoyl and substituted benzoyl.

The preferred "halo lower alkyl" group is trifluoromethyl.

The preferred "halo lower alkanoyl" group is trifluoroacetyl.

The compounds of this invention may be prepared by the general synthesis according to Scheme I:

Scheme I

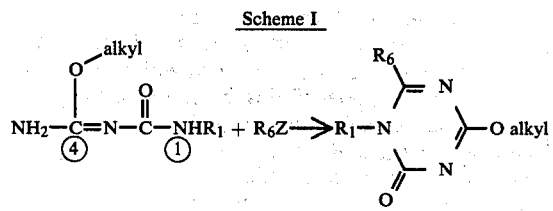

A 1-$R_1$-substituted-4-alkyl isobiuret is cyclized to the corresponding 1-$R_1$-6-$R_6$-4-alkoxy-1,2-dihydro-1,3,5-triazin-2-one by treatment with an $R_6$ substituted cyclizing reagent.

The group in the 4-position of the isobiuret, shown as O-alkyl, may be any suitable group which is capable of being displaced upon treatment of the cyclized product with a hydrazinyl reagent. The alkoxy groups, as shown in Scheme I, are preferred.

Condensation of the 4-alkoxy triazinone with an appropriately substituted hydrazine produces the 4-hydrazino adduct according to Scheme II:

Scheme II

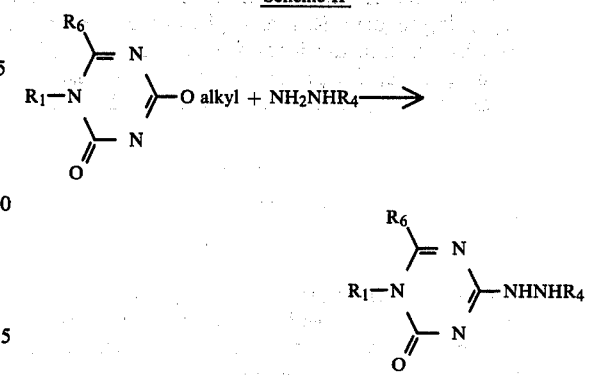

Alternatively, the 4-methoxy-s-triazinone may be reacted with unsubstituted hydrazine thereby producing the 4-hydrazinyl triazinone which may be treated with an appropriate alkylating or acylating reagent such as an alkyl halide, alkyl triflate, alkanoyl halide, such as, benzyol halide, methyl halide, acetyl chloride, benzoylchloride, and result in the desired $R_4$ substitution.

The triazinthione compounds according to this invention are prepared by the same general route by utilizing the corresponding isothiobiuret as starting material.

The isobiuret (isothiobiuret) starting material may be prepared by any manner known to those skilled in the art. One process for the synthesis of these particular isobiurets (isothiobiuret) comprises the treatment of an O-alkylisourea (isothiourea), such as O-methyl-isourea, with an appropriately substituted isocyanate (isothiocyanate) according to Scheme III:

Scheme III

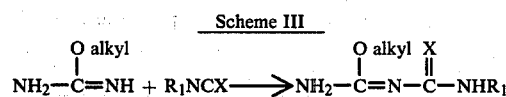

For example, O-methyl isourea may be prepared in situ by neutralizing O-methyl isourea hydrogen sulfate with one equivalent of base, such as sodium hydroxide, in a polar nonaqueous solvent, such as, THF or ethanol. The reaction media is dried before adding the isocyanate by addition of a drying agent such as sodium sulfate ($Na_2SO_4$). The isocyanate is added to the reaction media dropwise and the isobiuret recovered by extraction and recrystallization.

The isocyanate may be prepared from primary alkyl amines or anilines by methods known to those in the art (e.g., reaction with phosgene or thiophosgene in the customary manner).

The cyclizing reagent may consist of an activated form of an acid amide or ortho ester or acyl derivative such as a Vilsmier reagent which will bring about acylation and ring closure of the isobiuret or isothiobiuret to give the corresponding s-triazinone or thione of the type described above.

The cyclizing reagent employed in the reaction can be any cationic reagent system capable of generating in the reaction mixture a stabilized carbonium ion having the oxidation state of an acid or acid amide. Since the cationic carbon is incorporated into the ring the choice of reagent will determine the $R_6$ substitution in the compounds of Formula I above. Thus, in the case of a dialkyl carboxylic acid amide dialkyl acetal, such as, dialkyl formamide dialkyl acetal, $R_6$ is hydrogen and the resulting triazine is unsubstituted in the 6-position; in the case where the acetamide derivative is used as the cyclizing reagent, $R_6$ is methyl and the resulting triazine is substituted in the 6-position, and so on.

In general, the preferred cyclizing reagents are the ortho esters of carboxylic acids of the Formula V:

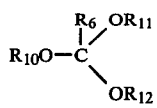

wherein: $R_6$ is hydrogen, or lower alkyl; and each of $R_{10}$ through $R_{12}$ are lower alkyl or halo lower alkyl. Exemplary ortho esters include triethylorthoformate and trimethylorthoacetate. Additional cyclizing reagents include the carboxylic acid amide dialkyl acetals, such as, dialkyl formamide dialkyl acetal, preferably, dimethyl formamide dimethyl acetal; dialkyl acetamide dialkyl acetals, preferably, dimethyl acetamide dimethyl acetal; dialkyl propionamide dialkyl acetal, preferably, dimethyl propionamide dimethyl acetal. Other carboxylic acid amide derivatives can also be used including substituted derivatives.

Other methylidene derivatives that can be used as the cyclizing reagent include the combination of an N,N-disubstituted carboxylic acid amide and any strong alkylating agent, preferably a strong methylating agent. Any of the strong alkylating agents known in the art such as methyliodide, methylfluorosulfonate, alkylmethane sulfonates, e.g., methylmethanesulfonate, and alkyl or dialkyl sulfates, e.g., dimethylsulfate can be suitably employed though dimethylsulfate is preferred owing to its ready availability. A cyclizing reagent of particular interest is a DMF-dimethylsulfate complex.

Reagents of the type shown in Formula V above are stable products which are commercially available or can be prepared in advance.

The cyclizing reaction can be carried out by simply combining the reactants in a suitable solvent at room temperature with stirring. The reaction time can be shortened by heating the reaction mixture or by using elevated pressure or both. The solvent selected should have a relatively high boiling point and low vapor pressure in order to permit the reaction mixture to be heated above 100° C. Dimethylformamide is a convenient solvent to use, particularly where the cyclizing reagent is a dimethylformamide derivative, though other organic solvents can also be used. The solvents that can be used include saturated and unsaturated hydrocarbons, aromatic solvents, alcohols such as methanol and ethanol, halogenated hydrocarbons such as chloroform, carbon tetrachloride, ethylene chloride, or others such as methyl acetate, ethyl acetate, acetonitrile, acetone, ether, acetamide, tetrahydrofuran and the like. Suitable mixtures of solvents can also be used. The reaction is preferably carried out under substantially anhydrous conditions though the presence of water can be tolerated. If small amounts of water are present, the effect can be offset by using an excess of the cyclizing reagent.

In carrying out the cyclizing reaction, the cyclizing reagent is preferably used in slight excess of the amount required as the stoichiometric equivalent of the isobiuret or isothiobiuret starting material. Reagent systems employing dimethyl sulfate are prepared as necessary for the cyclization or can be formed in situ in the reaction mixture by adding the reagent components to the reaction vessel in a suitable solvent or solvent mixture.

When carrying out the cyclizing reaction with a reagent of the type shown in Formula V, it is preferred to use as starting material an acid addition salt of the isobiuret or isothiobiuret or alternatively, if the free base is used, then an acid, preferably a mineral acid such as hydrochloric acid, can be added to the reaction mixture. When a reagent system comprising a carboxylic acid amide and a strong alkylating agent is employed, the reagent is itself acidic and the reaction proceeds readily with the free base as starting material. In such instances it may be advantageous to add a proton scavenging solvent such as a tertiary amine, e.g., triethylamine or cyclic amines such as pyridine. Other miscible solvents can be used along with the preferred amines e.g., solvents such as triethanolamine, acetonitrile, ethanol, etc., though dimethyl formamide is preferred.

The conversion of most isobiurets and isothiobiurets to the corresponding s-triazine derivative can be achieved in from less than about 20 minutes to about 5 hours at temperatures on the order of 100° C. to 120° C. Higher or lower temperatures can be used if desired, and the reaction can be carried out at room temperature.

In most cases the cyclized end product can be recovered by filtering after direct crystallization from the reaction mixture particularly where the solvent has been chosen to facilitate recovery of the end product. Where the product does not readily crystallize, the novel s-triazinone derivatives can be conveniently isolated in the pure form by solvent extraction using any of the usual organic solvents which are not miscible with water such as: the hydrocarbons, for example, hexane; the chlorinated hydrocarbons, for example, chloroform or carbon tetrachloride; the aromatic solvents such as benzene, xylene, toluene, o-chloro-toluene and the like; ethers such as dioxane; ketones such as 2-pentanone, etc. The s-triazinone product is extracted into the solvent layer generally after stripping the solvent or concentrating the reaction mixture then shaking with an extracting composition of water and solvent and removing the solvent component, leaving the by-product in the aqueous layer. The product is recovered by evaporating off the solvent. If desired, the product can be further purified by recrystallizing from a suitable organic solvent such as those noted above. The selection of solvent is not critical and generally those solvents which are most readily available will be employed.

The compounds of this invention may be readily converted to their nontoxic acid addition salts by customary methods in the art. The nontoxic salts of this invention are those salts the acid component of which is pharmacologically acceptable in the intended dosages. Such salts would include those prepared from inorganic acids, and organic acids, such as, higher fatty acids, high molecular weight acids, etc. Exemplary acids include hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

It is well known in the pharmacological arts that nontoxic acid addition salts of pharmacologically active amine compounds do not differ in activities from their free base. The salts merely provide a convenient solubility factor. Other salts, for example, quarternary ammonium salts, are prepared by known methods for quarternizing organic nitrogen compounds.

The following example shows the synthetic preparation of the hydrazinyl triazinone compounds described herein. It is to be construed as an illustration of the preparation of the compounds and not as limitations thereof.

EXAMPLE I

Preparation of
4-methylhydrazinyl-1-phenyl-1,2-dihydro-1,3,5-triazin-2-one

A. 4-Methyl-1-phenyl isobiuret 41.45 g of aqueous NaOH are added to a stirred suspension of O-methylisourea hydrogen sulfate (44.33 g) in 400 ml of THF while being cooled. After stirring at RT for 15 minutes, 200 g of anhydrous $Na_2SO_4$ are added to the reaction mixture with continued stirring for one hour. Phenyl isocyanate (31.30 g) dissolved in THF (150 ml) is then added dropwise over a period of two hours. The mixture is filtered, concentrated, and the product crystallized from ethylacetate and hexane, to afford 41.10 g of the isobiuret, m.p. 86°–88° C.

B. 4-Methoxy-1-phenyl-1,2-dihydro-1,3,5-triazin-2-one 4-methyl-1-phenyl isobiuret (41.08 g) is dissolved in 212 ml of triethylorthoformate. The solution is heated to 110°–115° C. for approximately four hours with a stream of $N_2$ being passed over the reaction mixture to flush out evolved ethanol and the reaction mixture allowed to cool overnight. The reaction product is filtered, washed with hexane, and recrystallized from toluene, affording 16.43 g of the triazinone, m.p. 171°–173° C.

C. 4-Methylhydrazinyl-1-phenyl-1,2-dihydro-1,3,5-triazin-2-one 2.4 ml of methylhydrazine dissolved in 10 ml of absolute ethanol are added to a suspension of 4-methoxy-1-phenyl-1,2-dihydro-1,3,5-triazin-2-one (4.60 g) in 100 ml of absolute ethanol and stirred for one hour. The solid product is filtered, washed with ether and dried to give 3.10 g (63.1%) of 4-methylhydrazino-1-phenyl-s-triazin-2-one, m.p. 219° C.

The isobiurets listed in Table II may be substituted for 4-methyl-1-phenyl isobiuret in Example 1 to prepare the corresponding 4-methoxy-s-triazinones in Table III.

TABLE II 4-methyl-1-benzyl isobiuret
4-methyl-1-(2-methylphenyl)-isobiuret
4-methyl-1-(2-ethylphenyl)-isobiuret
4-methyl-1-(2,6-dimethylphenyl)-isobiuret
4-methyl-1-(2,6-diethylphenyl)-isobiuret
4-methyl-1-(2-chlorophenyl)-isobiuret
4-methyl-1-(3-chlorophenyl)-isobiuret
4-methyl-1-(4-chlorophenyl)-isobiuret
4-methyl-1-(2-chloro-6-bromophenyl)-isobiuret
4-methyl-1-(3,4-dihydroxyphenyl)-isobiuret
4-methyl-1-(3,4-dichlorophenyl)-isobiuret
4-methyl-1-(3,4-dimethoxyphenyl)-isobiuret
4-methyl-1-(3,5-dichlorophenyl)-isobiuret
4-methyl-1-(3,4-diacetoxyphenyl)-isobiuret
4-methyl-1-(3,4-diethoxyphenyl)-isobiuret
4-methyl-1-(2-pyridyl)-isobiuret
4-methyl-1-(3-pyridyl)-isobiuret
4-methyl-1-(4-pyridyl)-isobiuret
4-methyl-1-[2-(3-methylpyridyl)]-isobiuret
4-methyl-1-[2-(4-methylpyridyl)]-isobiuret
4-methyl-1-[2-(5-methylpyridyl)]-isobiuret
4-methyl-1-[2-(5-methylpyridyl)]-isobiuret
4-methyl-1-[2-(3-chloropyridyl)]-isobiuret
4-methyl-1-[2-(4-chloropyridyl)]-isobiuret
4-methyl-1-[2-(3-carbomethoxypyridyl)]-isobiuret
4-methyl-1-[2-(3-cyanopyridyl)]-isobiuret
4-methyl-1-[2-(3-methoxypyridyl)]-isobiuret

TABLE III 4-methoxy-1-benzyl-1,2-dihydro-1,3,5-triazin-2-one
4-methoxy-1-(2-methylphenyl)-1,2-dihydro-1,3,5-triazin-2-one
4-methoxy-1-(2-ethylphenyl)-1,2-dihydro-1,3,5-triazin-2-one
4-methoxy-1-(2,6-dimethylphenyl)-1,2-dihydro-1,3,5-triazin-2-one
4-methoxy-1-(2,6-diethylphenyl)-1,2-dihydro-1,3,5-triazin-2-one
4-methoxy-1-(2-chlorophenyl)-1,2-dihydro-1,3,5-triazin-2-one
4-methoxy-1-(3-chlorophenyl)-1,2-dihydro-1,3,5-triazin-2-one
4-methoxy-1-(4-chlorophenyl)-1,2-dihydro-1,3,5-triazin-2-one
4-methoxy-1-(2-chloro-6-bromophenyl)-1,2,-dihydro-1,3,5-triazin-2-one
4-methoxy-1-(3,4-dihydroxyphenyl)-1,2-dihydro-1,3,5-triazin-2-one
4-methoxy-1-(3,4-dichlorophenyl)-1,2-dihydro-1,3,5-triazin-2-one
4-methoxy-1-(3,4-dimethoxyphenyl)-1,2-dihydro-1,3,5-triazin-2-one
4-methoxy-1-(3,5-dichlorophenyl)-1,2-dihydro-1,3,5-triazin-2-one
4-methoxy-1-(3,4-diacetoxyphenyl)-1,2-dihydro-1,3,5-triazin-2-one
4-methoxy-1-(3,4-diethoxyphenyl)-1,2-dihydro-1,3,5-triazin-2-one
4-methoxy-1-(2-pyridyl)-1,2-dihydro-1,3,5-triazin-2-one
4-methoxy-1-(3-pyridyl)-1,2-dihydro-1,3,5-triazin-2-one
4-methoxy-1-(4-pyridyl)-1,2-dihydro-1,3,5-triazin-2-one
4-methoxy-1-[2-(3-methylpyridyl)]-1,2-dihydro-1,3,5-triazin-2-one
4-methoxy-1-[2-(4-methylpyridyl)]-1,2-dihydro-1,3,5-triazin-2-one
4-methoxy-1-[2-(5-methylpyridyl)]-1,2-dihydro-1,3,5-triazin-2-one
4-methoxy-1-[2-(3-chloropyridyl)]-1,2-dihydro-1,3,5-triazin-2-one
4-methoxy-1-[2-(4-chloropyridyl)]-1,2-dihydro-1,3,5-triazin-2-one
4-methoxy-1-[2-(3-carbomethoxypyridyl)]-1,2-dihydro-1,3,5-triazin-2-one
4-methoxy-1-[2-(3-cyanopyridyl)]-1,2-dihydro-1,3,5-triazin-2-one
4-methoxy-1-[2-(3-methoxypyridyl)]-1,2-dihydro-1,3,5-triazin-2-one The 4-hydrazino-s-triazinones of Table IV may be prepared from the corresponding 4-methoxy-s-triazinones disclosed in Table III.

TABLE IV 4-hydrazino-1-benzyl-1,2-dihydro-1,3,5-triazin-2-one
4-hydrazino-1-(2-methylphenyl)-1,2-dihydro-1,3,5-triazin-2-one
4-hydrazino-1-(2-ethylphenyl)-1,2-dihydro-1,3,5-triazin-2-one 4-hydrazino-1-(2,6-dimethylphenyl)-1,2-dihydro-1,3,5-triazin-2-one
4-hydrazino-1-(2,6-diethylphenyl)-1,2-dihydro-1,3,5-triazin-2-one
4-hydrazino-1-(2-chlorophenyl)-1,2-dihydro-1,3,5-triazin-2-one
4-hydrazino-1-(3-chlorophenyl)-1,2-dihydro-1,3,5-triazin-2-one
4-hydrazino-1-(4-chlorophenyl)-1,2-dihydro-1,3,5-triazin-2-one
4-hydrazino-1-(2-chloro-6-bromophenyl)-1,2-dihydro-1,3,5-triazin-2-one
4-hydrazino-1-(3,4-dihydroxyphenyl)-1,2-dihydro-1,3,5-triazin-2-one
4-hydrazino-1-(3,4-dichlorophenyl)-1,2-dihydro-1,3,5-triazin-2-one
4-hydrazino-1-(3,4-dimethoxyphenyl)-1,2-dihydro-1,3,5-triazin-2-one
4-hydrazino-1-(3,5-dichlorophenyl)-1,2-dihydro-1,3,5-triazin-2-one
4-hydrazino-1-(3,4-diacetoxyphenyl)-1,2-dihydro-1,3,5-triazin-2-one
4-hydrazino-1-(3,4-diethoxyphenyl)-1,2-dihydro-1,3,5-triazin-2-one
4-hydrazino-1-(2-pyridyl)-1,2-dihydro-1,3,5-triazin-2-one
4-hydrazino-1-(3-pyridyl)-1,2-dihydro-1,3,5-triazin-2-one
4-hydrazino-1-(4-pyridyl)-1,2-dihydro-1,3,5-triazin-2-one
4-hydrazino-1-[2-(3-methylpyridyl)]-1,2-dihydro-1,3,5-triazin-2-one
4-hydrazino-1-[2-(4-methylpyridyl)]-1,2-dihydro-1,3,5-triazin-2-one
4-hydrazino-1-[2-(5-methylpyridyl)]-1,2-dihydro-1,3,5-triazin-2-one
4-hydrazino-1-[2-(3-chloropyridyl)]-1,2-dihydro-1,3,5-triazin-2-one
4-hydrazino-1-[2-(4-chloropyridyl)]-1,2-dihydro-1,3,5-triazin-2-one
4-hydrazino-1-[2-(3-carbomethoxypyridyl)]-1,2-dihydro-1,3,5-triazin-2-one
4-hydrazino-1-[2-(3-cyanopyridyl)]-1,2-dihydro-1,3,5-triazin-2-one
4-hydrazino-1-[2-(3-methoxypyridyl)]-1,2-dihydro-1,3,5-triazin-2-one
4-methylhydrazino-1-benzyl-1,2-dihydro-1,3,5-triazin-2-one
4-methylhydrazino-1-(2-methylphenyl)-1,2-dihydro-1,3,5-triazin-2-one
4-methylhydrazino-1-(2-ethylphenyl)-1,2-dihydro-1,3,5-triazin-2-one
4-methylhydrazino-1-(2,6-dimethylphenyl)-1,2-dihydro-1,3,5-triazin-2-one
4-methylhydrazino-1-(2,6-diethylphenyl)-1,2-dihydro-1,3,5-triazin-2-one
4-methylhydrazino-1-(2-chlorophenyl)-1,2-dihydro-1,3,5-triazin-2-one
4-methylhydrazino-1-(3-chlorophenyl)-1,2-dihydro-1,3,5-triazin-2-one
4-methylhydrazino-1-(4-chlorophenyl)-1,2-dihydro-1,3,5-triazin-2-one
4-methylhydrazino-1-(2-chloro-6-bromophenyl)-1,2-dihydro-1,3,5-triazin-2-one
4-methylhydrazino-1-(3,4-dihydroxyphenyl)-1,2-dihydro-1,3,5-triazin-2-one
4-methylhydrazino-1-(3,4-dichlorophenyl)-1,2-dihydro-1,3,5-triazin-2-one
4-methylhydrazino-1-(3,4-dimethoxyphenyl)-1,2-dihydro-1,3,5-triazin-2-one
4-methylhydrazino-1-(3,5-dichlorophenyl)-1,2-dihydro-1,3,5-triazin-2-one
4-methylhydrazino-1-(3,4-diacetoxyphenyl)-1,2-dihydro-1,3,5-triazin-2-one
4-methylhydrazino-1-(3,4-diethoxyphenyl)-1,2-dihydro-1,3,5-triazin-2-one
4-methylhydrazino-1-(2-pyridyl)-1,2-dihydro-1,3,5-triazin-2-one
4-methylhydrazino-1-(3-pyridyl)-1,2-dihydro-1,3,5-triazin-2-one
4-methylhydrazino-1-(4-pyridyl)-1,2-dihydro-1,3,5-triazin-2-one
4-methylhydrazino-1-[2-(3-methylpyridyl)]-1,2-dihydro-1,3,5-triazin-2-one
4-methylhydrazino-1-[2-(4-methylpyridyl)]-1,2-dihydro-1,3,5-triazin-2-one
4-methylhydrazino-1-[2-(5-methylpyridyl)]-1,2-dihydro-1,3,5-triazin-2-one
4-methylhydrazino-1-[2-(3-chloropyridyl)]-1,2-dihydro-1,3,5-triazin-2-one
4-methylhydrazino-1-[2-(4-chloropyridyl)]-1,2-dihydro-1,3,5-triazin-2-one
4-methylhydrazino-1-[2-chloro-6-bromophenyl)]-1,2-dihydro-1,3,5-triazin-2-one
4-methylhydrazino-1-[2-(3-cyanopyridyl)]-1,2-dihydro-1,3,5-triazin-2-one
4-methylhydrazino-1-[2-(3-methoxypyridyl)]-1,2-dihydro-1,3,5-triazin-2-one
4-acetylhydrazino-1-benzyl-1,2-dihydro-1,3,5-triazin-2-one
4-acetylhydrazino-1-(2-methylphenyl)-1,2-dihydro-1,3,5-triazin-2-one
4-acetylhydrazino-1-(2-ethylphenyl)-1,2-dihydro-1,3,5-triazin-2-one
4-acetylhydrazino-1-(2,6-dimethylphenyl)-1,2-dihydro-1,3,5-triazin-2-one
4-acetylhydrazino-1-(2,6-diethylphenyl)-1,2-dihydro-1,3,5-triazin-2-one
4-acetylhydrazino-1-(2-chlorophenyl)-1,2-dihydro-1,3,5-triazin-2-one
4-acetylhydrazino-1-(3-chlorophenyl)-1,2,-dihydro-1,3,5-triazin-2-one
4-acetylhydrazino-1-(4-chlorophenyl)-1,2-dihydro-1,3,5-triazin-2-one
4-acetylhydrazino-1-(2-chloro-6-bromophenyl)-1,2-dihydro-1,3,5-triazin-2-one
4-acetylhydrazino-1-(3,4-dihydroxyphenyl)-1,2-dihydro-1,3,5-triazin-2-one
4-acetylhydrazino-1-(3,4-dichlorophenyl)-1,2-dihydro-1,3,5-triazin-2-one
4-acetylhydrazino-1-(3,4-dimethoxyphenyl)-1,2-dihydro-1,3,5-triazin-2-one
4-acetylhydrazino-1-(3,5-dichlorophenyl)-1,2-dihydro-1,3,5-triazin-2-one
4-acetylhydrazino-1-(3,4-diacetoxyphenyl)-1,2-dihydro-1,3,5-triazin-2-one
4-acetylhydrazino-1-(3,4-diethoxyphenyl)-1,2-dihydro-1,3,5-triazin-2-one
4-acetylhydrazino-1-(2-pyridyl)-1,2-dihydro-1,3,5-triazin-2-one
4-acetylhydrazino-1-(3-pyridyl)-1,2-dihydro-1,3,5-triazin-2-one
4-acetylhydrazino-1-(4-pyridyl)-1,2-dihydro-1,3,5-triazin-2-one
4-acetylhydrazino-1-[2-(3-methylpyridyl)]-1,2-dihydro-1,3,5-triazin-2-one 4-acetylhydrazino-1-[2-(4-methylpyridyl)]-1,2-dihydro-1,3,5-triazin-2-one
4-acetylhydrazino-1-[2-(5-methylpyridyl)]-1,2-dihydro-1,3,5-triazin-2-one
4-acetylhydrazino-1-[2-(3-chloropyridyl)]-1,2-dihydro-1,3,5-triazin-2-one
4-acetylhydrazino-1-[2-(4-chloropyridyl)]-1,2-dihydro-1,3,5-triazin-2-one
4-acetylhydrazino-1-[2-(3-carbomethoxypyridyl)]-1,2-dihydro-1,3,5-triazin-2-one
4-acetylhydrazino-1-[2-(3-cyanopyridyl)]-1,2-dihydro-1,3,5-triazin-2-one
4-acetylhydrazino-1-[2-(3-methoxypyridyl)]-1,2-dihydro-1,3,5-triazin-2-one
4-trifluoromethylhydrazino-1-benzyl-1,2-dihydro-1,3,5-triazin-2-one
4-trifluoromethylhydrazino-1-(2-methylphenyl)-1,2-dihydro-1,3,5-triazin-2-one
4-trifluoromethylhydrazino-1-(2-ethylphenyl)-1,2-dihydro-1,3,5-triazin-2-one
4-trifluoromethylhydrazino-1-(2,6-dimethylphenyl)-1,2-dihydro-1,3,5-triazin-2-one
4-trifluoromethylhydrazino-1-(2,6-diethylphenyl)-1,2-dihydro-1,3,5-triazin-2-one
4-trifluoromethylhydrazino-1-(2-chlorophenyl)-1,2-dihydro-1,3,5-triazin-2-one
4-trifluoromethylhydrazino-1-(3-chlorophenyl)-1,2-dihydro-1,3,5-triazin-2-one
4-trifluoromethylhydrazino-1-(4-chlorophenyl)-1,2-dihydro-1,3,5-triazin-2-one
4-trifluoromethylhydrazino-1-(2-chloro-6-bromophenyl)-1,2-dihydro-1,3,5-triazin-2-one
4-trifluoromethylhydrazino-1-(3,4-dihydroxyphenyl)-1,2-dihydro-1,3,5-triazin-2-one
4-trifluoromethylhydrazino-1-(3,4-dichlorophenyl)-1,2-dihydro-1,3,5-triazin-2-one
4-trifluoromethylhydrazino-1-(3,4-dimethoxyphenyl)-1,2-dihydro-1,3,5-triazin-2-one
4-trifluoromethylhydrazino-1-(3,5-dichlorophenyl)-1,2-dihydro-1,3,5-triazin-2-one
4-trifluoromethylhydrazino-1-(3,4-diacetoxyphenyl)-1,2-dihydro-1,3,5-triazin-2-one
4-trifluoromethylhydrazino-1-(3,4-diethoxyphenyl)-1,2-dihydro-1,3,5-triazin-2-one
4-trifluoromethylhydrazino-1-(2-pyridyl)-1,2-dihydro-1,3,5-triazin-2-one
4-trifluorometylhydrazino-1-(3-pyridyl)-1,2-dihydro-1,3,5-triazin-2-one
4-trifluoromethylhydrazino-1-(4-pyridyl)-1,2-dihydro-1,3,5-triazin-2-one
4-trifluoromethylhydrazino-1-[2-(3-methylpyridyl)]-1,2-dihydro-1,3,5-triazin-2-one
4-trifluoromethylhydrazino-1-[2-(4-methylpyridyl)]-1,2-dihydro-1,3,5-triazin-2-one
4-trifluoromethylhydrazino-1-[2-(5-methylpyridyl)]-1,2-dihydro-1,3,5-triazin-2-one
4-trifluoromethylhydrazino-1-[2-(3-chloropyridyl)]-1,2-dihydro-1,3,5-triazin-2-one
4-trifluoromethylhydrazino-1-[2-(4-chloropyridyl)]-1,2-dihydro-1,3,5-triazin-2-one
4-trifluoromethylhydrazino-1-[2-(3-carbomethoxypyridyl)]-1,2-dihydro-1,3,5-triazin-2-one
4-trifluoromethylhydrazino-1-[2-(3-cyanopyridyl)]-1,2-dihydro-1,3,5-triazin-2-one
4-trifluoromethylhydrazino-1-[2-(3-methoxypyridyl)]-1,2-dihydro-1,3,5-triazin-2-one
4-phenylhydrazino-1-benzyl-1,2-dihydro-1,3,5-triazin-2-one
4-phenylhydrazino-1-(2-methylphenyl)-1,2-dihydro-1,3,5-triazin-2-one
4-phenylhydrazino-1-(2-ethylphenyl)-1,2-dihydro-1,3,5-triazin-2-one
4-phenylhydrazino-1-(2,6-dimethylphenyl)-1,2-dihydro-1,3,5-triazin-2-one
4-phenylhydrazino-1-(2,6-diethylphenyl)-1,2-dihydro-1,3,5-triazin-2-one
4-phenylhydrazino-1-(2-chlorophenyl)-1,2-dihydro-1,3,5-triazin-2-one
4-phenylhydrazino-1-(3-chlorophenyl)-1,2-dihydro-1,3,5-triazin-2-one
4-phenylhydrazino-1-(4-chlorophenyl)-1,2-dihydro-1,3,5-triazin-2-one
4-phenylhydrazino-1-(2-chloro-6-bromophenyl)-1,2-dihydro-1,3,5-triazin-2-one
4-phenylhydrazino-1-(3,4-dihydroxyphenyl)-1,2-dihydro-1,3,5-triazin-2-one
4-phenylhydrazino-1-(3,4-dichlorophenyl)-1,2-dihydro-1,3,5-triazin-2-one
4-phenylhydrazino-1-(3,4-dimethoxyphenyl)-1,2-dihydro-1,3,5-triazin-2-one
4-phenylhydrazino-1-(3,5-dichlorophenyl)-1,2-dihydro-1,3,5-triazin-2-one
4-phenylhydrazino-1-(3,4-diacetoxyphenyl)-1,2-dihydro-1,3,5-triazin-2-one
4-phenylhydrazino-1-(3,4-diethoxyphenyl)-1,2-dihydro-1,3,5-triazin-2-one
4-phenylhydrazino-1-(2-pyridyl)-1,2-dihydro-1,3,5-triazin-2-one
4-phenylhydrazino-1-(3-pyridyl)-1,2-dihydro-1,3,5-triazin-2-one
4-phenylhydrazino-1-(4-pyridyl)-1,2,-dihydro-1,3,5-triazin-2-one
4-phenylhydrazino-1-[2-(3-methylpyridyl)]-1,2-dihydro-1,3,5-triazin-2-one
4-phenylhydrazino-1-[2-(4-methylpyridyl)]-1,2-dihydro-1,3,5-triazin-2-one
4-phenylhydrazino-1-[2-(5-methylpyridyl)]-1,2-dihydro-1,3,5-triazin-2-one
4-phenylhydrazino-1-[2-(3-chloropyridyl)]-1,2-dihydro-1,3,5-triazin-2-one
4-phenylhydrazino-1-[2-(4-chloropyridyl)]-1,2-dihydro-1,3,5-triazin-2-one
4-phenylhydrazino-1-[2-(3-carbomethoxypyridyl)]-1,2-dihydro-1,3,5-triazin-2-one
4-phenylhydrazino-1-[2-(3-cyanopyridyl)]-1,2-dihydro-1,3,5-triazin-2-one
4-phenylhydrazino-1-[2-(3-methoxypyridyl)]-1,2-dihydro-1,3,5-triazin-2-one
4-benzylhydrazino-1-benzyl-1,2-dihydro-1,3,5-triazin-2-one
4-benzylhydrazino-1-(2-methylphenyl)-1,2-dihydro-1,3,5-triazin-2-one
4-benzylhydrazino-1-(2-ethylphenyl)-1,2-dihydro-1,3,5-triazin-2-one
4-benzylhydrazino-1-(2,6-dimethylphenyl)-1,2-dihydro-1,3,5-triazin-2-one
4-benzylhydrazino-1-(2,6-diethylphenyl)-1,2-dihydro-1,3,5-triazin-2-one
4-benzylhydrazino-1-(2-chlorophenyl)-1,2-dihydro-1,3,5-triazin-2-one
4-benzylhydrazino-1-(3-chlorophenyl)-1,2-dihydro-1,3,5-triazin-2-one
4-benzylhydrazino-1-(4-chlorophenyl)-1,2-dihydro-1,3,5-triazin-2-one
4-benzylhydrazino-1-(2-chloro-6-bromophenyl)-1,2-dihydro-1,3,5-triazin-2-one 4-benzylhydrazino-1-(3,4-dihydroxyphenyl)-1,2-dihydro-1,3,5-triazin-2-one
4-benzylhydrazino-1-(3,4-dichlorophenyl)-1,2-dihydro-1,3,5-triazin-2-one
4-benzylhydrazino-1-(3,4-dimethoxyphenyl)-1,2-dihydro-1,3,5-triazin-2-one
4-benzylhydrazino-1-(3,5-dichlorophenyl)-1,2-dihydro-1,3,5-triazin-2-one
4-benzylhydrazino-1-(3,4-diacetoxyphenyl)-1,2-dihydro-1,3,5-triazin-2-one
4-benzylhydrazino-1-(3,4-diethoxyphenyl)-1,2-dihydro-1,3,5-triazin-2-one
4-benzylhydrazino-1-(2-pyridyl)-1,2-dihydro-1,3,5-triazin-2-one
4-benzylhydrazino-1-(3-pyridyl)-1,2-dihydro-1,3,5-triazin-2-one
4-benzylhydrazino-1-(4-pyridyl)-1,2,-dihydro-1,3,5-triazin-2-one
4-benzylhydrazino-1-[2-(3-methylpyridyl)]-1,2-dihydro-1,3,5-triazin-2-one
4-benzylhydrazino-1-[2-(4-methylpyridyl)]-1,2-dihydro-1,3,5-triazin-2-one
4-benzylhydrazino-1-[2-(5-methylpyridyl)]-1,2-dihydro-1,3,5-triazin-2-one
4-benzylhydrazino-1-[2-(3-chloropyridyl)]-1,2-dihydro-1,3,5-triazin-2-one
4-benzylhydrazino-1-[2-(4-chloropyridyl)]-1,2-dihydro-1,3,5-triazin-2-one
4-benzylhydrazino-1-[2-(3-carbomethoxypyridyl)]-1,2-dihydro-1,3,5-triazin-2-one
4-benzylhydrazino-1-[2-(3-cyanopyridyl)]-1,2-dihydro-1,3,5-triazin-2-one
4-benzylhydrazino-1-[2-(3-methoxypyridyl)]-1,2-dihydro-1,3,5-triazin-2-one
4-allylhydrazino-1-benzyl-1,2-dihydro-1,3,5-triazin-2-one
4-allylhydrazino-1-(2-methylphenyl)-1,2-dihydro-1,3,5-triazin-2-one
4-allylhydrazino-1-(2-ethylphenyl)-1,2-dihydro-1,3,5-triazin-2-one
4-allylhydrazino-1-(2,6-dimethylphenyl)-1,2-dihydro-1,3,5-triazin-2-one
4-allylhydrazino-1-(2,6-diethylphenyl)-1,2-dihydro-1,3,5-triazin-2-one
4-allylhydrazino-1-(2-chlorophenyl)-1,2-dihydro-1,3,5-triazin-2-one
4-allylhydrazino-1-(3-chlorophenyl)-1,2-dihydro-1,3,5-triazin-2-one
4-allylhydrazino-1-(4-chlorophenyl)-1,2-dihydro-1,3,5-triazin-2-one
4-allylhydrazino-1-(2-chloro-6-bromophenyl)-1,2-dihydro-1,3,5-triazin-2-one
4-allylhydrazino-1-(3,4-dihydroxyphenyl)-1,2-dihydro-1,3,5-triazin-2-one
4-allylhydrazino-1-(3,4-dichlorophenyl)-1,2-dihydro-1,3,5-triazin-2-one
4-allylhydrazino-1-(3,4-dimethoxyphenyl)-1,2-dihydro-1,3,5-triazin-2-one
4-allylhydrazino-1-(3,5-dichlorophenyl)-1,2-dihydro-1,3,5-triazin-2-one
4-allylhydrazino-1-(3,4-diacetoxyphenyl)-1,2-dihydro-1,3,5-triazin-2-one
4-allylhydrazino-1-(3,4-diethoxyphenyl)-1,2-dihydro-1,3,5-triazin-2-one
4-allylhydrazino-1-(2-pyridyl)-1,2-dihydro-1,3,5-triazin-2-one
4-allylhydrazino-1-(3-pyridyl)-1,2-dihydro-1,3,5-triazin-2-one
4-allylhydrazino-1-(4-pyridyl)-1,2,-dihydro-1,3,5-triazin-2-one
4-allylhydrazino-1-[2-(3-methylpyridyl)]-1,2-dihydro-1,3,5-triazin-2-one
4-allylhydrazino-1-[2-(4-methylpyridyl)]-1,2-dihydro-1,3,5-triazin-2-one
4-allylhydrazino-1-[2-(5-methylpyridyl)]-1,2-dihydro-1,3,5-triazin-2-one
4-allylhydrazino-1-[2-(3-chloropyridyl)]-1,2-dihydro-1,3,5-triazin-2-one
4-allylhydrazino-1-[2-(4-chloropyridyl)]-1,2-dihydro-1,3,5-triazin-2-one
4-allylhydrazino-1-[2-(3-carbomethoxypyridyl)]-1,2-dihydro-1,3,5-triazin-2-one
4-allylhydrazino-1-[2-(3-cyanopyridyl)]-1,2-dihydro-1,3,5-triazin-2-one
4-allylhydrazino-1-[2-(3-methoxypyridyl)]-1,2-dihydro-1,3,5-triazin-2-one The general synthesis described above may be utilized to prepare the 4-hydrazino-triazinones in Table V.

TABLE V 4-hydrazino-6-methyl-1-phenyl-1,2-dihydro-1,3,5-triazin-2-one
4-methylhydrazino-6-methyl-1-phenyl-1,2-dihydro-1,3,5-triazin-2-one
4-ethylhydrazino-6-methyl-1-phenyl-1,2-dihydro-1,3,5-triazin-2-one
4-propylhydrazino-6-methyl-1-phenyl-1,2-dihydro-1,3,5-triazin-2-one
4-phenylhydrazino-6-methyl-1-phenyl-1,2-dihydro-1,3,5-triazin-2-one
4-benzylhydrazino-6-methyl-1-phenyl-1,2-dihydro-1,3,5-triazin-2-one
4-allylhydrazino-6-methyl-1-phenyl-1,2-dihydro-1,3,5-triazin-2-one
4-propargylhydrazino-6-methyl-1-phenyl-1,2-dihydro-1,3,5-triazin-2-one
4-pyridylhydrazino-6-methyl-1-phenyl-1,2-dihydro-1,3,5-triazin-2-one
4-hydrazino-6-methyl-1-(2-methylphenyl)-1,2-dihydro-1,3,5-triazin-2-one
4-methylhydrazino-6-methyl-1-(2-methylphenyl)-1,2-dihydro-1,3,5-triazin-2-one
4-ethylhydrazino-6-methyl-1-(2-methylphenyl)-1,2-dihydro-1,3,5-triazin-2-one
4-propylhydrazino-6-methyl-1-(2-methylphenyl)-1,2-dihydro-1,3,5-triazin-2-one
4-phenylhydrazino-6-methyl-1-(2-methylphenyl)-1,2-dihydro-1,3,5-triazin-2-one
4-benzylhydrazino-6-methyl-1-(2-methylphenyl)-1,2-dihydro-1,3,5-triazin-2-one
4-allylhydrazino-6-methyl-1-(2-methylphenyl)-1,2-dihydro-1,3,5-triazin-2-one
4-propargylhydrazino-6-methyl-1-(2-methylphenyl)-1,2-dihydro-1,3,5-triazin-2-one
4-pyridylhydrazino-6-methyl-1-(2-methylphenyl)-1,2-dihydro-1,3,5-triazin-2-one
4-hydrazino-6-methyl-1-(2-ethylphenyl)-1,2-dihydro-1,3,5-triazin-2-one
4-methylhydrazino-6-methyl-1-(2-ethylphenyl)-1,2-dihydro-1,3,5-triazin-2-one
4-ethylhydrazino-6-methyl-1-(2-ethylphenyl)-1,2-dihydro-1,3,5-triazin-2-one
4-propylhydrazino-6-methyl-1-(2-ethylphenyl)-1,2-dihydro-1,3,5-triazin-2-one
4-phenylhydrazino-6-methyl-1-(2-ethylphenyl)-1,2-dihydro-1,3,5-triazin-2-one 4-benzylhydrazino-6-methyl-1-(2-ethylphenyl)-1,2-dihydro-1,3,5-triazin-2-one
4-allylhydrazino-6-methyl-1-(2-ethylphenyl)-1,2-dihydro-1,3,5-triazin-2-one
4-propargylhydrazino-6-methyl-1-(2-ethylphenyl)-1,2-dihydro-1,3,5-triazin-2-one
4-pyridylhydrazino-6-methyl-1-(2-ethylphenyl)-1,2-dihydro-1,3,5-triazin-2-one
4-hydrazino-6-methyl-1-(2-chlorophenyl)-1,2-dihydro-1,3,5-triazin-2-one
4-methylhydrazino-6-methyl-1-(2-chlorophenyl)-1,2-dihydro-1,3,5-triazin-2-one
4-ethylhydrazino-6-methyl-1-(2-chlorophenyl)-1,2-dihydro-1,3,5-triazin-2-one
4-propylhydrazino-6-methyl-1-(2-chlorophenyl)-1,2-dihydro-1,3,5-triazin-2-one
4-phenylhydrazino-6-methyl-1-(2-chlorophenyl)-1,2-dihydro-1,3,5-triazin-2-one
4-benzylhydrazino-6-methyl-1-(2-chlorophenyl)-1,2-dihydro-1,3,5-triazin-2-one
4-allylhydrazino-6-methyl-1-(2-chlorophenyl)-1,2-dihydro-1,3,5-triazin-2-one
4-propargylhydrazino-6-methyl-1-(2-chlorophenyl)-1,2-dihydro-1,3,5-triazin-2-one
4-pyridylhydrazino-6-methyl-1-(2-chlorophenyl)-1,2-dihydro-1,3,5-triazin-2-one
4-hydrazino-6-methyl-1-(3,4-dimethoxyphenyl)-1,2-dihydro-1,3,5-triazin-2-one
4-methylhydrazino-6-methyl-1-(3,4-dimethoxyphenyl)-1,2-dihydro-1,3,5-triazin-2-one
4-ethylhydrazino-6-methyl-1-(3,4-dimethoxyphenyl)-1,2-dihydro-1,3,5-triazin-2-one
4-propylhydrazino-6-methyl-1-(3,4-dimethoxyphenyl)-1,2-dihydro-1,3,5-triazin-2-one
4-phenylhydrazino-6-methyl-1-(3,4-dimethoxyphenyl)-1,2-dihydro-1,3,5-triazin-2-one
4-benzylhydrazino-6-methyl-1-(3,4-dimethoxyphenyl)-1,2-dihydro-1,3,5-triazin-2-one
4-allylhydrazino-6-methyl-1-(3,4-dimethoxyphenyl)-1,2-dihydro-1,3,5-triazin-2-one
4-propargylhydrazino-6-methyl-1-(3,4-dimethoxyphenyl)-1,2-dihydro-1,3,5-triazin-2-one
4-pyridylhydrazino-6-methyl-1-(3,4-dimethoxyphenyl)-1,2-dihydro-1,3,5-triazin-2-one
4-hydrazino-6-methyl-1-(3,4-dihydroxyphenyl)-1,2-dihydro-1,3,5-triazin-2-one
4-methylhydrazino-6-methyl-1-(3,4-dihydroxyphenyl)-1,2-dihydro-1,3,5-triazin-2-one
4-ethylhydrazino-6-methyl-1-(3,4-dihydroxyphenyl)-1,2-dihydro-1,3,5-triazin-2-one
4-propylhydrazino-6-methyl-1-(3,4-dihydroxyphenyl)-1,2-dihydro-1,3,5-triazin-2-one
4-phenylhydrazino-6-methyl-1-(3,4-dihydroxyphenyl)-1,2-dihydro-1,3,5-triazin-2-one
4-benzylhydrazino-6-methyl-1-(3,4-dihydroxyphenyl)-1,2-dihydro-1,3,5-triazin-2-one
4-allylhydrazino-6-methyl-1-(3,4-dihydroxyphenyl)-1,2-dihydro-1,3,5-triazin-2-one
4-propargylhydrazino-6-methyl-(3,4-dihydroxyphenyl)-1,2-dihydro-1,3,5-triazin-2-one
4-pyridylhydrazino-6-methyl-1-(3,4-dihydroxyphenyl)-1,2-dihydro-1,3,5-triazin-2-one
4-hydrazino-6-methyl-1-(3-chlorophenyl)-1,2-dihydro-1,3,5-triazin-2-one
4-methylhydrazino-6-methyl-1-(3-chlorophenyl)-1,2-dihydro-1,3,5-triazin-2-one
4-ethylhydrazino-6-methyl-1-(3-chlorophenyl)-1,2-dihydro-1,3,5-triazin-2-one
4-propylhydrazino-6-methyl-1-(3-chlorophenyl)-1,2-dihydro-1,3,5-triazin-2-one
4-phenylhydrazino-6-methyl-1-(3-chlorophenyl)-1,2-dihydro-1,3,5-triazin-2-one
4-benzylhydrazino-6-methyl-1-(3-chlorophenyl)-1,2-dihydro-1,3,5-triazin-2-one
4-allylhydrazino-6-methyl-1-(3-chlorophenyl)-1,2-dihydro-1,3,5-triazin-2-one
4-propargylhydrazino-6-methyl-1-(3-chlorophenyl)-1,2-dihydro-1,3,5-triazin-2-one
4-pyridylhydrazino-6-methyl-1-(3-chlorophenyl)-1,2-dihydro-1,3,5-triazin-2-one
4-hydrazino-6-methyl-1-(4-chlorophenyl)-1,2-dihydro-1,3,5-triazin-2-one
4-methylhydrazino-6-methyl-1-(4-chlorophenyl)-1,2-dihydro-1,3,5-triazin-2-one
4-ethylhydrazino-6-methyl-1-(4-chlorophenyl)-1,2-dihydro-1,3,5-triazin-2-one
4-propylhydrazino-6-methyl-1-(4-chlorophenyl)-1,2-dihydro-1,3,5-triazin-2-one
4-phenylhydrazino-6-methyl-1-(4-chlorophenyl)-1,2-dihydro-1,3,5-triazin-2-one
4-benzylhydrazino-6-methyl-(4-chlorophenyl)-1,2-dihydro-1,3,5-triazin-2-one
4-allylhydrazino-6-methyl-(4-chlorophenyl)-1,2-dihydro-1,3,5-triazin-2-one
4-propargylhydrazino-6-methyl-(4-chlorophenyl)-1,2-dihydro-1,3,5-triazin-2-one
4-pyridylhydrazino-6-methyl-(4-chlorophenyl)-1,2-dihydro-1,3,5-triazin-2-one
4-hydrazino-6-methyl-1-(3,4-dichlorophenyl)-1,2-dihydro-1,3,5-triazin-2-one
4-methylhydrazino-6-methyl-1-(3,4-dichlorophenyl)-1,2-dihydro-1,3,5-triazin-2-one
4-ethylhydrazino-6-methyl-1-(3,4-dichlorophenyl)-1,2-dihydro-1,3,5-triazin-2-one
4-propylhydrazino-6-methyl-1-(3,4-dichlorophenyl)-1,2-dihydro-1,3,5-triazin-2-one
4-phenylhydrazino-6-methyl-1-(3,4-dichlorophenyl)-1,2-dihydro-1,3,5-triazin-2-one
4-benzylhydrazino-6-methyl-1-(3,4-dichlorophenyl)-1,2-dihydro-1,3,5-triazin-2-one
4-allylhydrazino-6-methyl-1-(3,4-dichlorophenyl)-1,2-dihydro-1,3,5-triazin-2-one
4-propargylhydrazino-6-methyl-1-(3,4-dichlorophenyl)-1,2-dihydro-1,3,5-triazin-2-one
4-pyridylhydrazino-6-methyl-1-(3,4-dichlorophenyl)-1,2-dihydro-1,3,5-triazin-2-one
4-hydrazino-6-methyl-1-(2,6-diethylphenyl)-1,2-dihydro-1,3,5-triazin-2-one
4-methylhydrazino-6-methyl-1-(2,6-diethylphenyl)-1,2-dihydro-1,3,5-triazin-2-one
4-ethylhydrazino-6-methyl-1-(2,6-diethylphenyl)-1,2-dihydro-1,3,5-triazin-2-one
4-propylhydrazino-6-methyl-1-(2,6-diethylphenyl)-1,2-dihydro-1,3,5-triazin-2-one
4-phenylhydrazino-6-methyl-1-(2,6-diethylphenyl)-1,2-dihydro-1,3,5-triazin-2-one
4-benzylhydrazino-6-methyl-1-(2,6-diethylphenyl)-1,2-dihydro-1,3,5-triazin-2-one
4-allylhydrazino-6-methyl-1-(2,6-diethylphenyl)-1,2-dihydro-1,3,5-triazin-2-one
4-propargylhydrazino-6-methyl-1-(2,6-diethylphenyl)-1,2-dihydro-1,3,5-triazin-2-one
4-pyridylhydrazino-6-methyl-1-(2,6-diethylphenyl)-1,2-dihydro-1,3,5-triazin-2-one
4-hydrazino-6-methyl-1-(2,6-dichlorophenyl)-1,2-dihydro-1,3,5-triazin-2-one 4-methylhydrazino-6-methyl-1-(2,6-dichlorophenyl)-1,2-dihydro-1,3,5-triazin-2-one
4-ethylhydrazino-6-methyl-1-(2,6-dichlorophenyl)-1,2-dihydro-1,3,5-triazin-2-one
4-propylhydrazino-6-methyl-1-(2,6-dichlorophenyl)-1,2-dihydro-1,3,5-triazin-2-one
4-phenylhydrazino-6-methyl-1-(2,6-dichlorophenyl)-1,2-dihydro-1,3,5-triazin-2-one
4-benzylhydrazino-6-methyl-1-(2,6-dichlorophenyl)-1,2-dihydro-1,3,5-triazin-2-one
4-allylhydrazino-6-methyl-1-(2,6-dichlorophenyl)-1,2-dihydro-1,3,5-triazin-2-one
4-propargylhydrazino-6-methyl-1-(2,6-dichlorophenyl)-1,2-dihydro-1,3,5-triazin-2-one
4-pyridylhydrazino-6-methyl-1-(2,6-dichlorophenyl)-1,2-dihydro-1,3,5-triazin-2-one
4-hydrazino-6-ethyl-1-phenyl-1,2-dihydro-1,3,5-triazin-2-one
4-methylhydrazino-6-ethyl-1-phenyl-1,2-dihydro-1,3,5-triazin-2-one
4-ethylhydrazino-6-ethyl-1-phenyl-1,2-dihydro-1,3,5-triazin-2-one
4-propylhydrazino-6-ethyl-1-phenyl-1,2-dihydro-1,3,5-triazin-2-one
4-phenylhydrazino-6-ethyl-1-phenyl-1,2-dihydro-1,3,5-triazin-2-one
4-benzylhydrazino-6-ethyl-1-phenyl-1,2-dihydro-1,3,5-triazin-2-one
4-allylhydrazino-6-ethyl-1-phenyl-1,2-dihydro-1,3,5-triazin-2-one
4-propargylhydrazino-6-ethyl-1-phenyl-1,2-dihydro-1,3,5-triazin-2-one
4-pyridylhydrazino-6-ethyl-1-phenyl-1,2-dihydro-1,3,5-triazin-2-one
4-hydrazino-6-ethyl-1-(2-methylphenyl)-1,2-dihydro-1,3,5-triazin-2-one
4-methylhydrazino-6-ethyl-1-(2-methylphenyl)-1,2-dihydro-1,3,5-triazin-2-one
4-ethylhydrazino-6-ethyl-1-(2-methylphenyl)-1,2-dihydro-1,3,5-triazin-2-one
4-propylhydrazino-6-ethyl-1-(2-methylphenyl)-1,2-dihydro-1,3,5-triazin-2-one
4-phenylhydrazino-6-ethyl-1-(2-methylphenyl)-1,2-dihydro-1,3,5-triazin-2-one
4-benzylhydrazino-6-ethyl-1-(2-methylphenyl)-1,2-dihydro-1,3,5-triazin-2-one
4-allylhydrazino-6-ethyl-1-(2-methylphenyl)-1,2-dihydro-1,3,5-triazin-2-one
4-propargylhydrazino-6-ethyl-1-(2-methylphenyl)-1,2-dihydro-1,3,5-triazin-2-one
4-pyridylhydrazino-6-ethyl-1-(2-methylphenyl)-1,2-dihydro-1,3,5-triazin-2-one
4-hydrazino-6-ethyl-1-(2-ethylphenyl)-1,2-dihydro-1,3,5-triazin-2-one
4-methylhydrazino-6-ethyl-1-(2-ethylphenyl)-1,2-dihydro-1,3,5-triazin-2-one
4-ethylhydrazino-6-ethyl-1-(2-ethylphenyl)-1,2-dihydro-1,3,5-triazin-2-one
4-propylhydrazino-6-ethyl-1-(2-ethylphenyl)-1,2-dihydro-1,3,5-triazin-2-one
4-phenylhydrazino-6-ethyl-1-(2-ethylphenyl)-1,2-dihydro-1,3,5-triazin-2-one
4-benzylhydrazino-6-ethyl-1-(2-ethylphenyl)-1,2-dihydro-1,3,5-triazin-2-one
4-allylhydrazino-6-ethyl-1-(2-ethylphenyl)-1,2-dihydro-1,3,5-triazin-2-one
4-propargylhydrazino-6-ethyl-1-(2-ethylphenyl)-1,2-dihydro-1,3,5-triazin-2-one
4-pyridylhydrazino-6-ethyl-1-(2-ethylphenyl)-1,2-dihydro-1,3,5-triazin-2-one
4-hydrazino-6-ethyl-1-(2-chlorophenyl)-1,2-dihydro-1,3,5-triazin-2-one
4-methylhydrazino-6-ethyl-1-(2-chlorophenyl)-1,2-dihydro-1,3,5-triazin-2-one
4-ethylhydrazino-6-ethyl-1-(2-chlorophenyl)-1,2-dihydro-1,3,5-triazin-2-one
4-propylhydrazino-6-ethyl-1-(2-chlorophenyl)-1,2-dihydro-1,3,5-triazin-2-one
4-phenylhydrazino-6-ethyl-1-(2-chlorophenyl)-1,2-dihydro-1,3,5-triazin-2-one
4-benzylhydrazino-6-ethyl-1-(2-chlorophenyl)-1,2-dihydro-1,3,5-triazin-2-one
4-allylhydrazino-6-ethyl-1-(2-chlorophenyl)-1,2-dihydro-1,3,5-triazin-2-one
4-propargylhydrazino-6-ethyl-1-(2-chlorophenyl)-1,2-dihydro-1,3,5-triazin-2-one
4-pyridylhydrazino-6-ethyl-1-(2-chlorophenyl)-1,2-dihydro-1,3,5-triazin-2-one
4-hydrazino-6-ethyl-1-(4-chlorophenyl)-1,2-dihydro-1,3,5-triazin-2-one
4-methylhydrazino-6-ethyl-1-(4-chlorophenyl)-1,2-dihydro-1,3,5-triazin-2-one
4-ethylhydrazino-6-ethyl-1-(4-chlorophenyl)-1,2-dihydro-1,3,5-triazin-2-one
4-propylhydrazino-6-ethyl-1-(4-chlorophenyl)-1,2-dihydro-1,3,5-triazin-2-one
4-phenylhydrazino-6-ethyl-1-(4-chlorophenyl)-1,2-dihydro-1,3,5-triazin-2-one
4-benzylhydrazino-6-ethyl-1-(4-chlorophenyl)-1,2-dihydro-1,3,5-triazin-2-one
4-allylhydrazino-6-ethyl-1-(4-chlorophenyl)-1,2-dihydro-1,3,5-triazin-2-one
4-propargylhydrazino-6-ethyl-1-(4-chlorophenyl)-1,2-dihydro-1,3,5-triazin-2-one
4-pyridylhydrazino-6-ethyl-1-(4-chlorophenyl)-1,2-dihydro-1,3,5-triazin-2-one
4-hydrazino-6-ethyl-1-(3,4-dichlorophenyl)-1,2-dihydro-1,3,5-triazin-2-one
4-methylhydrazino-6-ethyl-1-(3,4-dichlorophenyl)-1,2-dihydro-1,3,5-triazin-2-one
4-ethylhydrazino-6-ethyl-1-(3,4-dichlorophenyl)-1,2-dihydro-1,3,5-triazin-2-one
4-propylhydrazino-6-ethyl-1-(3,4-dichlorophenyl)-1,2-dihydro-1,3,5-triazin-2-one
4-phenylhydrazino-6-ethyl-1-(3,4-dichlorophenyl)-1,2-dihydro-1,3,5-triazin-2-one
4-benzylhydrazino-6-ethyl-1-(3,4-dichlorophenyl)-1,2-dihydro-1,3,5-triazin-2-one
4-allylhydrazino-6-ethyl-1-(3,4-dichlorophenyl)-1,2-dihydro-1,3,5-triazin-2-one
4-propargylhydrazino-6-ethyl-1-(3,4-dichlorophenyl)-1,2-dihydro-1,3,5-triazin-2-one
4-pyridylhydrazino-6-ethyl-1-(3,4-dichlorophenyl)-1,2-dihydro-1,3,5-triazin-2-one
4-propargylhydrazino-6-ethyl-1-phenyl-1,2-dihydro-1,3,5-triazin-2-one
4-pyridylhydrazino-6-ethyl-1-phenyl-1,2-dihydro-1,3,5-triazin-2-one
4-hydrazino-6-ethyl-1-(3-chlorophenyl)-1,2-dihydro-1,3,5-triazin-2-one
4-methylhydrazino-6-ethyl-1-(3-chlorophenyl)-1,2-dihydro-1,3,5-triazin-2-one
4-ethylhydrazino-6-ethyl-1-(3-chlorophenyl)-1,2-dihydro-1,3,5-triazin-2-one
4-propylhydrazino-6-ethyl-1-(3-chlorophenyl)-1,2-dihydro-1,3,5-triazin-2-one 4-phenylhydrazino-6-ethyl-1-(3-chlorophenyl)-1,2-dihydro-1,3,5-triazin-2-one
4-benzylhydrazino-6-ethyl-1-(3-chlorophenyl)-1,2-dihydro-1,3,5-triazin-2-one
4-allylhydrazino-6-ethyl-1-(3-chlorophenyl)-1,2-dihydro-1,3,5-triazin-2-one
4-propargylhydrazino-6-ethyl-1-(3-chlorophenyl)-1,2-dihydro-1,3,5-triazin-2-one
4-pyridylhydrazino-6-ethyl-1-(3-chlorophenyl)-1,2-dihydro-1,3,5-triazin-2-one
4-hydrazino-6-ethyl-1-(3,4-ditrifluoroacetoxyphenyl)-1,2-dihydro-1,3,5-triazin-2-one
4-methylhydrazino-6-ethyl-1-(3,4-ditrifluoroacetoxyphenyl)-1,2-dihydro-1,3,5-triazin-2-one
4-ethylhydrazino-6-ethyl-1-(3,4-ditrifluoroacetoxyphenyl)-1,2-dihydro-1,3,5-triazin-2-one
4-propylhydrazino-6-ethyl-1-(3,4-ditrifluoroacetoxyphenyl)-1,2-dihydro-1,3,5-triazin-2-one
4-phenylhydrazino-6-ethyl-1-(3,4-ditrifluoroacetoxyphenyl)-1,2-dihydro-1,3,5-triazin-2-one
4-benzylhydrazino-6-ethyl-1-(3,4-ditrifluoroacetoxyphenyl)-1,2-dihydro-1,3,5-triazin-2-one
4-allylhydrazino-6-ethyl-1-(3,4-ditrifluoroacetoxyphenyl)-1,2-dihydro-1,3,5-triazin-2-one
4-propargylhydrazino-6-ethyl-1-(3,4-ditrifluoroacetoxyphenyl)-1,2-dihydro-1,3,5-triazin-2-one
4-pyridylhydrazino-6-ethyl-1-(3,4-ditrifluoroacetoxyphenyl)-1,2-dihydro-1,3,5-triazin-2-one
4-hydrazino-6-ethyl-1-(2,6-dimethylphenyl)-1,2-dihydro-1,3,5-triazin-2-one
4-methylhydrazino-6-ethyl-1-(2,6-dimethylphenyl)-1,2-dihydro-1,3,5-triazin-2-one
4-ethylhydrazino-6-ethyl-1-(2,6-dimethylphenyl)-1,2-dihydro-1,3,5-triazin-2-one
4-propylhydrazino-6-ethyl-1-(2,6-dimethylphenyl)-1,2-dihydro-1,3,5-triazin-2-one
4-phenylhydrazino-6-ethyl-1-(2,6-dimethylphenyl)-1,2-dihydro-1,3,5-triazin-2-one
4-benzylhydrazino-6-ethyl-1-(2,6-dimethylphenyl)-1,2-dihydro-1,3,5-triazin-2-one
4-allylhydrazino-6-ethyl-1-(2,6-dimethylphenyl)-1,2-dihydro-1,3,5-triazin-2-one
4-propargylhydrazino-6-ethyl-1-(2,6-dimethylphenyl)-1,2-dihydro-1,3,5-triazin-2-one
4-pyridylhydrazino-6-ethyl-1-(2,6-dimethylphenyl)-1,2-dihydro-1,3,5-triazin-2-one
4-hydrazino-6-ethyl-1-(2,6-diethylphenyl)-1,2-dihydro-1,3,5-triazin-2-one
4-methylhydrazino-6-ethyl-1-(2,6-diethylphenyl)-1,2-dihydro-1,3,5-triazin-2-one
4-ethylhydrazino-6-ethyl-1-(2,6-diethylphenyl)-1,2-dihydro-1,3,5-triazin-2-one
4-propylhydrazino-6-ethyl-1-(2,6-diethylphenyl)-1,2-dihydro-1,3,5-triazin-2-one
4-phenylhydrazino-6-ethyl-1-(2,6-diethylphenyl)-1,2-dihydro-1,3,5-triazin-2-one
4-benzylhydrazino-6-ethyl-1-(2,6-diethylphenyl)-1,2-dihydro-1,3,5-triazin-2-one
4-allylhydrazino-6-ethyl-1-(2,6-diethylphenyl)-1,2-dihydro-1,3,5-triazin-2-one
4-propargylhydrazino-6-ethyl-1-(2,6-diethylphenyl)-1,2-dihydro-1,3,5-triazin-2-one
4-pyridylhydrazino-6-ethyl-1-(2,6-diethylphenyl)-1,2-dihydro-1,3,5-triazin-2-one
4-hydrazino-6-ethyl-1-(2,6-dichlorophenyl)-1,2-dihydro-1,3,5-triazin-2-one
4-methylhydrazino-6-ethyl-1-(2,6-dichlorophenyl)-1,2-dihydro-1,3,5-triazin-2-one
4-ethylhydrazino-6-ethyl-1-(2,6-dichlorophenyl)-1,2-dihydro-1,3,5-triazin-2-one
4-propylhydrazino-6-ethyl-1-(2,6-dichlorophenyl)-1,2-dihydro-1,3,5-triazin-2-one
4-phenylhydrazino-6-ethyl-1-(2,6-dichlorophenyl)-1,2-dihydro-1,3,5-triazin-2-one
4-benzylhydrazino-6-ethyl-1-(2,6-dichlorophenyl)-1,2-dihydro-1,3,5-triazin-2-one
4-allylhydrazino-6-ethyl-1-(2,6-dichlorophenyl)-1,2-dihydro-1,3,5-triazin-2-one
4-propargylhydrazino-6-ethyl-1-(2,6-dichlorophenyl)-1,2-dihydro-1,3,5-triazin-2-one
4-pyridylhydrazino-6-ethyl-1-(2,6-dichlorophenyl)-1,2-dihydro-1,3,5-triazin-2-one The hydrazinyl compounds which possess blood pressure-lowering activity can be used as antihypertensive agents by oral, parenteral or rectal administration. Orally they may be administered as tablets, aqueous or oily suspensions, dispersible powders or granules, emulsions, hard or soft capsules, or syrups or elixers. Parenterally they may be administered as a salt in solution which pH is adjusted to physiologically accepted values. Aqueous solutions are preferred.

Compositions intended for oral use may be prepared according to any method known to the art for the manufacture of pharmaceutical compositions, and such compositions may contain one or more inert carrier agents including excipients, such as, sweetening agents, flavoring agents, coloring agents, preserving agents and the like, in order to provide a pharmaceutically elegant and palatable preparation.

The dosage regimen in carrying out the methods of this invention is that which ensures maximum therapeutic response until improvement is obtained, and thereafter the minimum effective level which gives relief. Thus, in general, the dosages are those that are therapeutically effective in the alleviation of hypertensive disorders. The therapeutically effective doses correspond to those dosage amounts found effective in tests using animal models which are known to correlate to human activity. In general, it is expected that daily doses between about 5 mg/kg and about 300 mg/kg (preferably in the range of about 10 to about 50 mg/kg/day), will be sufficient to produce the desired therapeutic effect, bearing in mind, of course, that in selecting the appropriate dosage in any specific case, consideration must be given to the patient's weight, general health, age, the severity of the disorder, and other factors which may influence response to the drug.

Various tests in animals have been carried out to show the ability of the compounds of this invention to exhibit reactions that can be correlated with activity in humans. These tests involve such factors as their blood pressure-lowering effect and determination of their toxicity. It has been found that the preferred compounds of this invention, when tested in the above situation, show a marked blood pressure-lowering activity.

Determination of Antihypertensive Activity

A description of the test protocol used in the determination of the antihypertensive activity of the compounds of this invention follows:

(a) Male TAC spontaneously hypertensive rats (SHR's), eleven weeks old, weighing 200–220 grams, are chosen for testing. The average systolic blood pressure (as measured below) should be 165 mmHg or above. Any rat not initially meeting this criterion is not utilized.

(b) A Beckman dynograph is balanced and calibrated using a Beckman indirect blood pressure coupler. A mercury monometer is placed on one arm of the glass "T" tube. The known pressure head in the tail cuff is synchronized with the recorder output so that 1 mm pen deflection=5 mmHg. Any correction is made using the chart calibration screw on the pressure coupler. The pulse amplitude is controlled by the pre-amplifier using a 20 v/cm setting.

The rats are prewarmed in groups of five for twenty minutes to dilate the tail artery from which the arterial pulse is recorded. After prewarming, each rat is placed in an individual restraining cage with continued warming. When the enclosure temperature has been maintained at 35° C. for 5 minutes, recordings are started. The tail cuff is placed on the rat's tail and the rubber bulb of the pneumatic tail cuff transducer is taped securely to the dorsal surface of the tail. When the rat's pulse reaches maximum amplitude and is unwavering, the cuff is inflated and the air slowly released. A reading of systolic blood pressure is read at the point of the chart when the first deflection appears on the chart recording while the air in the cuff is being released. The exact point of the systolic blood pressure reading is where the first deflection forms a 90° angle to the falling cuff pressure base line. After obtaining nine or ten consistent readings, the average of the middle five readings is calculated.

(c) Three groups of twenty rats receive the test compound at doses of about 25 mg/kg per os.

A fourth group of twenty control rats receive distilled water. Statistical comparisons of systolic pressure (four hours ater the first dose and sixteen hours after the second dose) are made on a daily basis using the Student t test for dependent variables (see, E. Lord, *Biometrika*, 34, 56 (1947)), with the predose observations serving as baseline values for each rat.

This testing method is known to correlate well with antihypertensive activity in humans and is a standard test used to determine antihypertensive properties. Accordingly, hydrazine triazinones which show effectiveness in the test can be considered to be active antihypertensive agents in humans.

We claim:

1. A compound of the formula

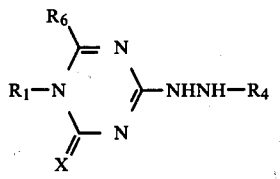

wherein:
X is oxygen or sulfur;
$R_1$ is phenyl, substituted phenyl, phenyl lower alkyl, or substituted phenyl lower alkyl;
$R_4$ is hydrogen, lower alkyl, lower alkanoyl, carboloweralkoxy, phenyl, or benzoyl;
$R_6$ is hydrogen or lower alkyl; and wherein:
substituted phenyl or substituted phenyl lower alkyl means a phenyl group or a phenyl lower alkyl group, respectively, in which one or more of the phenyl hydrogens has been replaced by the same or different substituents selected from the group consisting of halo, lower alkyl, halo lower alkyl, amino, lower alkanoyl, lower alkyl acylamino, hydroxy, carboloweralkoxy, phenyl lower alkoxy, lower alkyl acyloxy, cyano, halo lower alkoxy or lower alkyl sulfonyl;
and the pharmaceutically acceptable acid addition salts thereof.

2. A compound of the formula

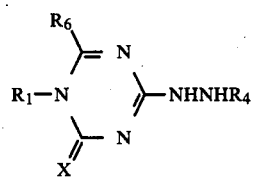

wherein:
X is oxygen or sulfur;
$R_1$ is phenyl or phenyl in which one or more of the phenyl hydrogens has been replaced by the same or different substituents selected from the group consisting of halo, lower alkyl, and halo lower alkyl;
$R_4$ is hydrogen, lower alkyl, carboloweralkoxy, phenyl, benzoyl, or lower alkanoyl;
$R_6$ is hydrogen; and the pharmaceutically acceptable acid addition salts thereof.

3. A compound of the formula

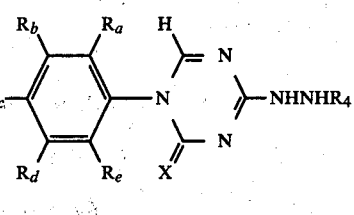

wherein:
X is oxygen or sulfur;
$R_4$ is hydrogen, lower alkanoyl, carboloweralkoxy, or benzoyl;
$R_a$, $R_b$, $R_c$, $R_d$ and $R_e$ are hydrogen, halo, or halo lower alkyl;
provided that $R_a$ and $R_e$ are not both halo when $R_4$ is lower alkanoyl; and further provided that neither $R_b$ nor $R_d$ are trihaloloweralkyl when $R_4$ is hydrogen; and the pharmaceutically acceptable acid addition salts thereof.

4. A compound according to the formula

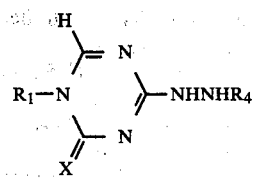

wherein:
X is oxygen or sulfur;
$R_1$ is phenyl;
$R_4$ is hydrogen, lower alkyl, carboloweralkoxy, lower alkanoyl, phenyl or benzoyl; and the pharmaceutically acceptable acid addition salts thereof.

5. A compound according to the formula

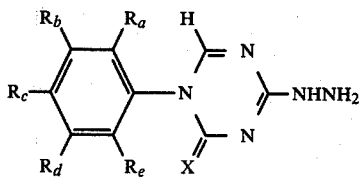

wherein:

X is oxygen or sulfur;

$R_a$, $R_b$, $R_c$, $R_d$ and $R_e$ are hydrogen, halo or lower alkyl; and the pharmaceutically acceptable acid addition salts thereof.

6. A compound according to the formula

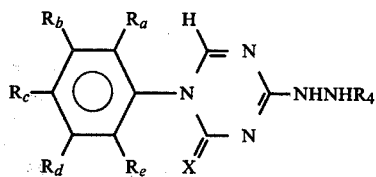

wherein:

X is oxygen or sulfur;

$R_4$ is carboloweralkoxy, benzoyl, or lower alkanoyl;

$R_a$ and $R_e$ are hydrogen, lower alkyl or trihaloloweralkyl;

$R_b$ and $R_d$ are hydrogen, halo, lower alkyl, or trihaloloweralkyl; and $R_c$ is hydrogen, halo or trihaloloweralkyl; and the pharmaceutically acceptable acid addition salts thereof.

7. A blood pressure lowering compound selected from the group consisting of:

4-acetylhydrazino-1-phenyl-1,2-dihydro-1,3,5-triazin-2-one;
4-ethoxycarbonylhydrazino-1-phenyl-1,2-dihydro-1,3,5-triazin-2-one;
4-hydrazino-1-phenyl-1,2-dihydro-1,3,5-triazin-2-one;
4-methylhydrazino-1-phenyl-1,2-dihydro-1,3,5-triazin-2-one;
4-acetylhydrazino-1-(4-chlorophenyl)-1,2-dihydro-1,3,5-triazin-2-one;
4-benzoylhydrazino-1-(4-chlorophenyl)-1,2-dihydro-1,3,5-triazin-2-one;
1-(3-chlorophenyl)-4-hydrazino-1,2-dihydro-1,3,5-triazin-2-one;
1-(3-chlorophenyl)-4-methylhydrazino-1,2-dihydro-1,3,5-triazin-2-one;
4-hydrazino-1-(4-methylphenyl)-1,2-dihydro-1,3,5-triazin-2-one;
1-(4-methylphenyl)-4-phenylhydrazino-1,2-dihydro-1,3,5-triazin-2-one;
1-(2,6-dichlorophenyl)-4-hydrazino-1,2-dihydro-1,3,5-triazin-2-one;
4-acetylhydrazino-1-(2-chlorophenyl)-1,2-dihydro-1,3,5-triazin-2-one;
1-(2-chlorophenyl)-4-hydrazino-1,2-dihydro-1,3,5-triazin-2-one;
1-(4-chlorophenyl)-4-ethoxycarbonyl-hydrazino-1,2-dihydro-1,3,5-triazin-2-one;
1-(4-chloropheynyl)-4-hydrazino-1,2-dihydro-1,3,5-triazin-2-one;
1-(4-chlorophenyl)-4-methylhydrazino-1,2-dihydro-1,3,5-triazin-2-one;
4-acetylhydrazino-1-(3-chlorophenyl)-1,2-dihydro-1,3,5-triazin-2-one;
1-(3,4-dichlorophenyl)-4-hydrazino-1,2-dihydro-1,3,5-triazin-2-one;
4-acetylhydrazino-1-(3-dichlorophenyl)-1,2-dihydro-1,3,5-triazin-2-one;
4-methylhydrazino-1-(3-trifluoromethyl-phenyl)-1,2-dihydro-1,3,5-triazin-2-one;
4-acetylhydrazino-1-(3-trifluoromethyl-(phenyl)-1,2-dihydro-1,3,5-triazin-2-one;
4-hydrazino-6-methyl-1-phenyl-1,2-dihydro-1,3,5-triazin-2-one;
1-(4-methylphenyl)-4-phenylhydrazino-1,2-dihydro-1,3,5-triazin-2-one; and
1-(4-methoxyphenyl)-4-phenylhydrazino-1,2-dihydro-1,3,5-triazin-2-one.

8. A method of lowering blood pressure in humans and other animals, comprising administering thereto an effective blood pressure lowering amount of a compound of the formula according to claim 1.

* * * * *